United States Patent
Pandiella Alonso et al.

(10) Patent No.: US 10,568,899 B2
(45) Date of Patent: Feb. 25, 2020

(54) COMBINATIONS OF A MITHRAMYCIN ANALOGUE AND ANOTHER CHEMOTHERAPEUTIC AGENT FOR THE TREATMENT OF TRIPLE NEGATIVE BREAST CANCER

(71) Applicant: ENTRECHEM, S.L., Oviedo (ES)

(72) Inventors: Atanasio Pandiella Alonso, Salamanca (ES); Alberto Ocaña Fernández, Albacete (ES); Francisco Morís Varas, Oviedo (ES)

(73) Assignee: ENTRECHEM, S.L., Oviedo (ES)

( * ) Notice: Subject to any disclaimer, the term of this patent is extended or adjusted under 35 U.S.C. 154(b) by 144 days.

(21) Appl. No.: 15/760,850

(22) PCT Filed: Sep. 16, 2016

(86) PCT No.: PCT/EP2016/072079
§ 371 (c)(1),
(2) Date: Mar. 16, 2018

(87) PCT Pub. No.: WO2017/046403
PCT Pub. Date: Mar. 23, 2017

(65) Prior Publication Data
US 2019/0350951 A1   Nov. 21, 2019

(30) Foreign Application Priority Data

Sep. 17, 2015  (EP) .................................. 15185746

(51) Int. Cl.
| | | |
|---|---|---|
| A61K 31/704 | (2006.01) | |
| A61K 31/337 | (2006.01) | |
| A61P 35/00 | (2006.01) | |
| A61K 31/506 | (2006.01) | |
| A61K 31/475 | (2006.01) | |
| A61K 31/7068 | (2006.01) | |

(52) U.S. Cl.
CPC .......... *A61K 31/704* (2013.01); *A61K 31/337* (2013.01); *A61K 31/475* (2013.01); *A61K 31/506* (2013.01); *A61K 31/7068* (2013.01); *A61P 35/00* (2018.01)

(58) Field of Classification Search
None
See application file for complete search history.

(56) References Cited

U.S. PATENT DOCUMENTS 8,772,253 B2   7/2014   Núñez González et al.
2005/0192432 A1   9/2005   Rohr et al.

FOREIGN PATENT DOCUMENTS

EP   2380909 A1   10/2011
EP   2457921 A2   5/2012

OTHER PUBLICATIONS

Shipitsin, M. et al., Molecular definition of breast tumor heterogeneity. Cancer Cell 2007; 11: 259-273.
Hanahan, D. and Weinberg, R.A., Hallmarks of cancer: the next generation. Cell 2011; 144: 646-674.
Perou, C.M. et al., Molecular portraits of human breast tumours. Nature 2000; 406: 747-752.
Sørlie, T. et al., Gene expression patterns of breast carcinomas distinguish tumor subclasses with clinical implications. Proc. Natl. Acad. Sci. U.S.A. 2001; 98: 10869-10874.
Nielsen T.O. et al., Immunohistochemical and clinical characterization of the basal-like subtype of invasive breast carcinoma. Clin. Cancer Res. 2004; 10: 5367-5374.
Lehmann, B.D. et al., Identification of human triple-negative breast cancer subtypes and preclinical models for selection of targeted therapies. J. Clin. Invest. (2011) 121:2750-2767.
Masuda, H. et al., Differential response to neoadjuvant chemotherapy among 7 triple-negative breast cancer molecular subtypes. Clin. Cancer Res. (2013) 19:5533-5540.
Carey, L. et al., Triple-negative breast cancer: disease entity or title of convenience? Nat. Rev. Clin. Oncol. (2010) 7:683-692.
Metzger-Filho, O. et al., Dissecting the heterogeneity of triple-negative breast cancer. J. Clin. Oncol. (2012) 30(15):1879-1887.
Dent, R. et al., Triple-negative breast cancer: clinical features and patterns of recurrence. Clin. Cancer Res. (2007) 13:4429-4434.

(Continued)

*Primary Examiner* — Layla D Berry
(74) *Attorney, Agent, or Firm* — Tristan A. Fuierer; Olive Law Group, PLLC (57) ABSTRACT

A composition comprising:
a) a compound of Formula (I),

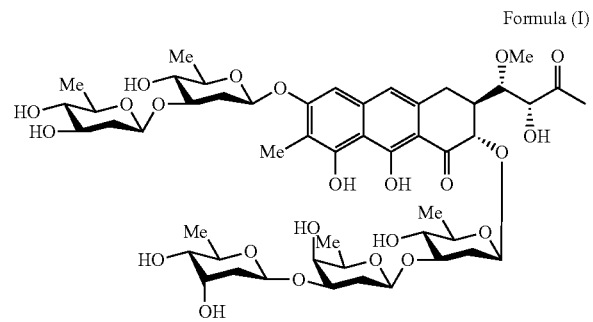

Formula (I)

or a salt, co-crystal or solvate thereof; and
b) at least one chemotherapeutic agent, or a salt, co-crystal or solvate thereof, suitable for use in the treatment of breast cancer, preferably triple negative breast cancer.

8 Claims, 6 Drawing Sheets

(56) References Cited

OTHER PUBLICATIONS

Bauer, J.A. et al., RNA interference (RNAi) screening approach identifies agents that enhance paclitaxel activity in breast cancer cells. Breast Cancer Res. (2010) 12:R41.
Widemann, B.C., Mithramycin for Children and Adults With Solid Tumors or Ewing Sarcoma. ClinicalTrials.gov NCT01610570.
Núñez, L.E. et al., A Novel Mithramycin Analogue with High Antitumor Activity and Less Toxicity Generated by Combinatorial Biosynthesis. J. Med. Chem. (2012) 55:5813-5825—Abstract Only.
Neve, R.M. et al., A collection of breast cancer cell lines for the study of functionally distinct cancer subtypes. Cancer Cell. (2006) 10:515-527.
Montero, J.C. et al., Active kinase profiling, genetic and pharmacological data define mTOR as an important common target in triple-negative breast cancer Oncogene (2014) 33:148-156.
Yuste, L. et al., Activation of ErbB2 by Overexpression or by Transmembrane Neuregulin Results in Differential Signaling and Sensitivity to Herceptin. Cancer Res. (2005) 65:6801-6810.
Montero, J.C. et al., Predominance of mTORC1 over mTORC2 in the Regulation of Proliferation of Ovarian Cancer Cells: Therapeutic Implications. Mol. Cancer Ther. (2012) 11:1342-1352.
Chou, T.C. and Talalay, P., Quantitative analysis of dose-effect relationships: the combined effects of multiple drugs or enzyme inhibitors. Adv. Enzyme Regul. (1984) 22:27-55.
Pandiella, A. et al., Antitumor activity of the novel mithramycin analog EC8042 in triple negative breast cancer. Cancer Res. (2012) 72:P4-06-17—Abstract Only.
Pandiella, A. et al., Action of EC8042 in triple-negative breast cancer. Therapeutic Implications. Mol. Cancer Ther (2011) 10:B39—Abstract Only.
Fernández-Guizán, A. et al., The activity of a novel mithramycin analog is related to its binding to DNAI cellular accumulation, and inhibition of Sp1-driven gene transcription. Chem. Biol. Interact. (2014) 219:123-132.
Vizcaíno, C. et al., Novel mithramycins abrogate the involvement of protein factors in the transcription of cell cycle control genes. Biochemical Pharmacology (2012) 84:1133-1142.
Pandiella, A. et al., Antitumoral activity of the mithralog EC-8042 in triple negative breast cancer linked to cell cycle arrest in G2. Oncotarget (2015) 6:32856-32867.
Méndez, C. et al., Expanding the Chemical Diversity of the Antitumoral Compound Mithramycin by Combinatorial Biosynthesis and Biocatalysis: The Quest for Mithralogs with Improved Therapeutic Window. Planta Med (2015) 81:1326-1338.
EntreChem's mithralogs show increased potency and higher selectivity for treatment of sarcoma. http://entrechem.com/en/news/2012/02.html.

COMBINATIONS OF A MITHRAMYCIN ANALOGUE AND ANOTHER CHEMOTHERAPEUTIC AGENT FOR THE TREATMENT OF TRIPLE NEGATIVE BREAST CANCER

CROSS-REFERENCE TO RELATED APPLICATIONS

This application is filed under the provisions of 35 U.S.C. § 371 and claims the priority of International Patent Application No. PCT/EP2016/072079, filed on 16 Sep. 2016 entitled "COMBINATIONS OF A MITHRAMYCIN ANALOGUE AND ANOTHER CHEMOTHERAPEUTIC AGENT FOR THE TREATMENT OF TRIPLE NEGATIVE BREAST CANCER" in the name of Atanasio PANDIELLA ALONSO et al., which claims priority to European Application No. 15185746.3 filed on 17 Sep. 2015, both of which are hereby incorporated by reference herein in their entirety.

FIELD OF THE INVENTION

The present invention relates to the provision of a composition comprising a) a mithramycin analogue; and b) at least one chemotherapeutic agent. The present invention additionally relates to use of said composition in the prevention and/or treatment of triple negative breast cancer. Furthermore, the present invention also discloses a pharmaceutical composition comprising the aforementioned composition and a method for its production.

BACKGROUND TO THE INVENTION

Breast cancer is a heterogeneous disease as demonstrated at a genomic level with the description of different breast cancer subtypes with independent clinical outcome [Cancer Cell 2007; 11: 259-273, Cell 2011; 144: 646-674, Nature 2000; 406: 747-752, Proc. Natl. Acad. Sci. U.S.A. 2001; 98: 10869-10874]. Among them, triple negative breast cancer (TNBC) refers to breast cancer that lacks detectable expression of hormone receptors and no Her2/neu (HER2) gene amplification. In particular, TNBC refers to breast cancer that lacks expression of the estrogen receptor (ER), the progesterone receptor (PR) and the HER2 receptor [Clin. Cancer Res. 2004; 10: 5367-5374].

TNBC is an aggressive form of breast cancer and represents 15% of all breast tumors. By using gene expression analyses it has been classified into seven subtypes with different sensitivities to treatment [J. Clin. Invest. (2011) 121:2750-2767; Clin. Cancer Res. (2013) 19:5533-5540]. Although the identification of these different subtypes represents a major advance in cancer, unfortunately the implementation of this classification for therapeutic purposes is unclear [J. Clin. Invest. (2011) 121:2750-2767]. Therefore, available therapeutic options for patients with TNBC are restricted to standard treatment with chemotherapy, typically based on taxane-, *vinca* alkaloid- or platinum-based compounds, which are only likely to be effective within the limitations of such chemotherapy in this type of tumor because of their rapid proliferation rates and frequent derangements in DNA repair mechanisms [Nat. Rev. Clin. Oncol. (2010) 7:683-692]. Unfortunately, relapses are frequent, and resistance to the chemotherapeutic agents is often encountered in the metastatic setting and the prognosis of TNBC patients is poor due to the limited therapeutic options and the lack of specific targeted agents [J. Clin. Oncol. (2012) 30(15):1879-1887; Clin. Cancer Res. (2007) 13:4429-4434]. These facts, together with the relatively poor knowledge of the driver molecular alterations present in TNBC, have stimulated identification of aberrant signaling networks that may be pharmacologically attacked in TNBC.

Mithramycin was recently identified as an agent able to sensitize TNBC cells to the antitumoral effect of taxanes, while RNAi screening for agents that enhance paclitaxel activity in TNBC [Breast Cancer Res. (2010) 12:R41]. In this regard, mithramycin was synergistic with paclitaxel in the two paclitaxel-sensitive lines MDA-MB-468 and MDA-MB-231 (average CI value of 0.66 and 0.54, respectively), and in the paclitaxel-resistant cell line HDQP1 (average CI value of 0.87). However, mithramycin and paclitaxel were antagonistic, average CI values significantly >1, in reducing cell viability at high effective drug doses ($IC_{50}$ and $IC_{25}$) in the paclitaxel-resistant lines CAL120, SW527 and MT3 (FIG. 4B). Collectively these data indicate that novel drug combinations with paclitaxel can effectively reduce cell viability of select paclitaxel-sensitive and importantly, paclitaxel-resistant TNBC cell lines. Mithramycin is a reversible DNA binding antitumoral antibiotic approved since 1970 by the FDA, although severe side effects have limited its use in the clinic. Recently, promising in vitro and in vivo activity linked to specific modes of action have triggered its clinical evaluation in Ewing sarcoma, lung, esophagus and other chest cancers [ClinicalTrials.gov NCT01610570]. Proteins whose expression is affected by this drug include various protooncogenes, proteins involved in angiogenesis or anti-apoptotic processes, p53-mediated transcriptional responses, as well as multidrug resistant gene 1 (MDR-1).

It is therefore the problem of the present invention to provide improved means of preventing and/or treating TNBC, which provides an anti-proliferative, tumor-specific effect, without adverse side effects.

BRIEF DESCRIPTION OF THE INVENTION

The present invention relates to a composition comprising:
a) a compound of Formula (I), Formula (I)

or a salt, co-crystal or solvate thereof; and
b) at least one chemotherapeutic agent, or a salt, co-crystal or solvate thereof.

Throughout the present specification the compound of Formula (I) is referred to as F(I).

In another preferred embodiment of the present invention, the at least one chemotherapeutic agent is a chemotherapeutic agent used for breast cancer, preferably selected from anti-mitotic chemotherapeutic agents, nucleoside analog chemotherapeutic agents or tyrosine kinase inhibitors.

In yet another preferred embodiment of the present invention, the at least one chemotherapeutic agent is an anti-mitotic chemotherapeutic agent selected from taxanes, more preferably an anti-mitotic chemotherapeutic agent selected from docetaxel, paclitaxel, docosahexaenoic acid-paclitaxel, polyglutamate-paclitaxel and angiopep-paclitaxel.

In still another preferred embodiment of the present invention, the at least one chemotherapeutic agent is a nucleoside analog chemotherapeutic agent selected from gemcitabine, cytarabine, fluorouracil and vidarabine.

In a further preferred embodiment of the present invention, the at least one chemotherapeutic agent is a tyrosine kinase inhibitor selected from dasatinib, imatinib, nilotinib, bosutinib, ponatinib, bafetinib, gefitinib, erlotinib and sunitinib.

In a yet more preferred embodiment of the composition of the present invention, the molar ratio of the compound of the Formula (I) to the at least one chemotherapeutic agent is from 1:0.01 to 1:500.

In a further preferred embodiment of the present invention, the at least one chemotherapeutic agent is vinorelbine, wherein the molar ratio of the compound of the Formula (I) to vinorelbine is 1:0.3.

The present invention also relates to a composition, as described herein, for use as a medicament, preferably in the prevention and/or treatment of breast cancer, more preferably triple-negative breast cancer, in a patient.

In addition, the present invention also relates to a use of a composition, as described herein, in the manufacture of a medicament for the prevention and/or treatment of disease, preferably breast cancer, more preferably triple-negative breast cancer.

Furthermore, the present invention relates to a method for producing a pharmaceutical composition, as described herein, which comprises mixing:
a) a compound of Formula (I), or a salt, co-crystal or solvate thereof, as described herein; and
b) at least one chemotherapeutic agent, or a salt, co-crystal or solvate thereof.

Moreover, the present invention relates to a kit-of-parts for use in treating triple negative breast cancer comprising:
a) a compound of Formula (I), Formula (I)

or a salt, co-crystal or solvate thereof; and
b) at least one chemotherapeutic agent, or a salt, co-crystal or solvate thereof.

Additionally, the present invention relates to a compound of Formula (I), Formula (I)

or a salt, co-crystal or solvate thereof; and
at least one chemotherapeutic agent, or a salt, co-crystal or solvate thereof,
for use in a method of treating triple negative breast cancer, wherein said compound of Formula (I), or a salt, co-crystal or solvate thereof, and said at least one chemotherapeutic agent, or a salt, co-crystal or solvate thereof are administered simultaneously, separately or sequentially from each other.

Analogously, the present invention relates to a method of administration of:
a) a compound of Formula (I), Formula (I)

or a salt, co-crystal or solvate thereof; and
b) at least one chemotherapeutic agent, or a salt, co-crystal or solvate thereof,
for treating triple negative breast cancer, wherein said compound of Formula (I), or a salt, co-crystal or solvate thereof, and said at least one chemotherapeutic agent, or a salt, co-crystal or solvate thereof are administered simultaneously, separately or sequentially from each other.

A last embodiment of the invention is to provide a method of prevention and/or treatment of patients suffering from breast cancer, preferably triple-negative breast cancer, which comprises the administration to a patient in need of or to a subject with risk of suffering from breast cancer, preferably triple-negative breast cancer, of an effective dose or amount of the combination of active compounds of the invention or of a composition comprising the same, particularly represented by the combination of a compound of Formula (I), or a salt, co-crystal or solvate thereof, with at least one chemotherapeutic agent, or a salt, co-crystal or solvate thereof, wherein the at least one chemotherapeutic agent is an anti-mitotic chemotherapeutic agent selected from taxanes, more preferably selected from docetaxel, paclitaxel, docosahexaenoic acid-paclitaxel, polyglutamate-paclitaxel and angiopep-paclitaxel, furthermore preferably docetaxel; a nucleoside analog chemotherapeutic agent selected from gemcitabine, cytarabine, fluorouracil and vidarabine, more preferably gemcitabine; or a tyrosine kinase inhibitor selected from dasatinib, imatinib, nilotinib, bosutinib, ponatinib, bafetinib, gefitinib, erlotinib and sunitinib, more preferably dasatinib.

DETAILED DESCRIPTION OF THE INVENTION

The present invention relates to a composition comprising:
a) a compound of Formula (I), Formula (I)

or a salt, co-crystal or solvate thereof; and
b) at least one chemotherapeutic agent, or a salt, co-crystal or solvate thereof.

Preferably, said composition is a pharmaceutical composition.

The compound of Formula (I) is also known as demycarosyl-3D-β-D-digitoxosyl-mithramycin SK and is referred to herein as F(I). The compound of Formula (I) may be obtained from genetically modified bacteria by combinatorial biosynthesis, specifically by fermentation of *Streptomyces argillaceus* M3W1-pMP*3BII [J. Med. Chem. (2012) 55:5813-5825]. The compound of Formula (I) is currently under development as antitumor agent due to the fact that it inhibits replication and transcription processes during macromolecular biosynthesis, by virtue of its affinity towards GC-rich DNA regions located at the minor groove of DNA, especially the site of union of the Sp1 transcription factor. Consequently, proteins whose expression is affected by this drug include various protooncogenes, proteins involved in angiogenesis or antiapoptotic processes, p53-mediated transcriptional responses, as well as multidrug resistant gene 1 (MDR-1). The compound of Formula (I) is 10 times less toxic than mithramycin in vivo, and therefore has a greater therapeutic window while it is active both in vitro and in cancer xenograft models.

In another preferred embodiment, the present invention comprises a composition, according to any of the foregoing, wherein the at least one chemotherapeutic agent is a chemotherapeutic agent suitable for use in treating breast cancer. In a further preferred embodiment, the at least one chemotherapeutic agent is selected from anti-mitotic chemotherapeutic agents, nucleoside analog chemotherapeutic agents or tyrosine kinase inhibitors.

In other preferred embodiments of the present invention, the composition comprises at least one chemotherapeutic agent, wherein said at least one chemotherapeutic agent is:
a) an anti-mitotic chemotherapeutic agent selected from taxanes and *vinca* alkaloids, more preferably an anti-mitotic chemotherapeutic agent selected from docetaxel, paclitaxel, vinorelbine, vinblastine, vindesine, vincristine, docosahexaenoic acid-paclitaxel, polyglutamate-paclitaxel and angiopep-paclitaxel;
b) a nucleoside analog chemotherapeutic agent selected from gemcitabine, cytarabine, fluorouracil and vidarabine; and/or
c) a tyrosine kinase inhibitor selected from dasatinib, nilotinib, bosutinib, ponatinib, bafetinib, imatinib, gefitinib, erlotinib and sunitinib.

In another preferred embodiment, the present invention comprises a composition according to any of the foregoing, wherein the at least one chemotherapeutic agent is docetaxel or vinorelbine. In yet another preferred embodiment, the present invention comprises a composition, according to any of the foregoing, wherein the at least one chemotherapeutic agent is gemcitabine. In still another preferred embodiment, the present invention comprises a composition, according to any of the foregoing, wherein the at least one chemotherapeutic agent is dasatinib.

Even more preferably, the at least one chemotherapeutic agent, according to any of the foregoing, is selected from docetaxel, gemcitabine or dasatinib. Alternatively, the at least one chemotherapeutic agent, according to any of the foregoing, may also be selected from docetaxel or gemcitabine.

Thus, one preferred embodiment relates to a composition comprising:
a) a compound of Formula (I); and
b) at least one chemotherapeutic agent selected from docetaxel, paclitaxel, vinorelbine, vinblastine, vindesine, vincristine, docosahexaenoic acid-paclitaxel, polyglutamate-paclitaxel, angiopep-paclitaxel, gemcitabine, cytarabine, fluorouracil, vidarabine, dasatinib, nilotinib, bosutinib or ponatinib.

Another preferred embodiment relates to a composition comprising:
a) a compound of Formula (I); and
b) at least one chemotherapeutic agent selected from docetaxel, paclitaxel, gemcitabine, cytarabine, fluorouracil, dasatinib or nilotinib, more preferably docetaxel, gemcitabine, fluorouracil, dasatinib or nilotinib, furthermore preferably docetaxel, gemcitabine or dasatinib.

In a particularly preferred embodiment of the foregoing composition of the invention, the molar ratio of the compound of the Formula (I) to the at least one chemotherapeutic agent is from 1:0.01 to 1:500. Preferably, the molar ratio of the compound of the Formula (I) to the at least one chemotherapeutic agent is from 1:0.05 to 1:200, more preferably 1:0.1 to 1:100, still more preferably 1:0.1 to 1:50. In a particularly preferred embodiment of the foregoing, the present invention relates to a composition comprising a compound of the Formula (I) and at least one chemotherapeutic agent, wherein said at least one chemotherapeutic agent is:
a) the anti-mitotic chemotherapeutic agent, docetaxel, wherein the molar ratio of the compound of the Formula (I) to said anti-mitotic chemotherapeutic agent is from 1:0.05 to 1:1, yet more preferably 1:0.1 to 1:0.5;
b) the nucleoside analog chemotherapeutic agent, gemcitabine, wherein the molar ratio of the compound of the Formula (I) to said nucleoside analog chemotherapeutic agent is from 1:0.1 to 1:2, yet more preferably 1:0.1 to 1:1; and/or
c) the tyrosine kinase inhibitor, dasatinib, wherein the molar ratio of the compound of the Formula (I) to said tyrosine kinase inhibitor is from 1:0.1 to 1:2, yet more preferably 1:0.1 to 1.1.

In another particularly preferred embodiment of the foregoing, the present invention relates to a composition comprising a compound of the Formula (I) and vinorelbine, wherein the molar ratio of the compound of the Formula (I) to vinorelbine is 1:0.3.

The composition of the present invention is preferably a pharmaceutical composition and more preferably comprises an excipient and/or carrier, wherein the excipient and/or carrier is selected from a diluent, bulking agent, filler, anti-adherent, binder, coating, colour, disintegrant, flavour, glidant, lubricant, preservative, sorbent, sweetener or vehicle. Such a composition can be in crystalline, powder, granular, compacted solid, liquid, solution, suspension, elixir, syrup, emulsion, cream, gel, droplet, mist, vapor or spray form.

Moreover, the composition of the invention is preferably comprised in a sealed container, more preferably a sealed container selected from a cavity/pocket of a blister pack, capsule, ampoule, sachet, bottle, vial, syringe or nebulizer or combinations thereof, more preferably, said container is a cavity/pocket of a blister pack, a capsule, an ampoule, a bottle or a syringe, furthermore preferably a cavity/pocket of a blister pack, an ampoule or a bottle, most preferably a cavity/pocket of a blister pack.

The present invention also relates to a composition, according to any of the foregoing, for use as a medicament. Furthermore, the present invention also relates to a composition, according to any of the foregoing, for use in the prevention and/or treatment of breast cancer in a patient. In other words, the present invention also relates to the use of a composition, according to any of the foregoing, in the manufacture of a medicament for the prevention and/or treatment of breast cancer. Analogously, the present invention also relates to a method of treatment of a patient using a composition, according to any of the foregoing, more preferably a method of treatment of breast cancer, yet more preferably a method of treatment of breast cancer in a synergic fashion. Preferably, said breast cancer is triple-negative breast cancer (TNBC). TNBC refers to a breast cancer that does not express the genes for the estrogen receptor, progesterone receptor and Her2/neu. Such a diagnosis may be made clinically.

The composition of the present invention may be administered according to the above molar ratios wherein the amount of the compound of the Formula (I) is between 0.01 and 1000 mg/kg bodyweight/dose, preferably between 0.1 and 100 mg/kg bodyweight/dose, more preferably between 1 and 10 mg/kg bodyweight/dose. Said dose may be administered (i) in a single daily dose, (ii) divided into n smaller doses which are administered at n intervals throughout the day, whereby n is a number between 2 and 5, preferably between 2 and 3, or (iii) accumulated for m days, whereby said accumulated dose is administered once every m days, whereby m is an interval of between 2 and 7 days, preferably between 3 and 5 days.

The patient is preferably a human or other mammal, preferably a human adult patient, more preferably a human adult female patient.

The present invention also relates to a method for producing any of the aforementioned composition, which comprises mixing:
a) a compound of Formula (I), or a salt, co-crystal or solvate thereof, according to the foregoing; and
b) at least one chemotherapeutic agent, or a salt, co-crystal or solvate thereof.

Said method may additionally involve a step of heating, agitation, centrifugation and/or filtration in order to ensure homogeneity of the resulting mixture. Said method may additionally comprise a packaging step, such that the aforementioned composition is comprised in a capsule, tablet, pill, caplet, ampoule, sachet, syringe, cartridge, nebulizer or other container.

Moreover, the present invention also relates to a kit-of-parts for use in treating triple negative breast cancer, preferably in a synergic fashion, comprising:
a) a compound of Formula (I), as described in the foregoing, or a salt, co-crystal or solvate thereof; and
b) at least one chemotherapeutic agent, as described in the foregoing, or a salt, co-crystal or solvate thereof.

In the kit-of-parts, said compound of Formula (I) and said at least one chemotherapeutic agent are preferably comprised in separate compositions and/or containers. Said compositions are preferably pharmaceutical compositions and more preferably each independently comprise an excipient and/or carrier, wherein the excipient and/or carrier is selected from a diluent, bulking agent, filler, anti-adherent, binder, coating, colour, disintegrant, flavour, glidant, lubricant, preservative, sorbent, sweetener or vehicle. Moreover, such compositions can be in crystalline, powder, granular, compacted solid, liquid, solution, suspension, elixir, syrup, emulsion, cream, gel, droplet, mist, vapor or spray form. Said container is preferably a sealable container selected from a cavity/pocket of a blister pack, capsule, ampoule, sachet, bottle, vial, syringe or nebulizer or combinations thereof, more preferably, said container is a cavity/pocket of a blister pack, a capsule, an ampoule, a bottle or a syringe, furthermore preferably a cavity/pocket of a blister pack, an ampoule or a bottle, most preferably a cavity/pocket of a blister pack, wherein when the compound of Formula (I) and at least one chemotherapeutic agent, or salts, co-crystals or solvates thereof are each comprised in separate cavities/pockets of a blister pack, said separate cavities/pockets are part of the same blister pack or part of different blister packs.

Furthermore, the present invention relates to a mode of administration involving a compound of Formula (I), as described in the foregoing, or a salt, co-crystal or solvate thereof; and at least one chemotherapeutic agent, as described in the foregoing, or a salt, co-crystal or solvate thereof, for use in a method of treating triple negative breast cancer, preferably in a synergic fashion, wherein said compound of Formula (I), or a salt, co-crystal or solvate thereof, and said at least one chemotherapeutic agent, or a salt, co-crystal or solvate thereof are administered simultaneously, separately or sequentially from each other.

Analogously, the present invention relates to a method of administration of:
a) a compound of Formula (I), as described in the foregoing, or a salt, co-crystal or solvate thereof; and
b) at least one chemotherapeutic agent, as described in the foregoing, or a salt, co-crystal or solvate thereof,
for treating triple negative breast cancer, preferably in a synergic fashion, wherein said compound of Formula (I), or a salt, co-crystal or solvate thereof, and said at least one chemotherapeutic agent, or a salt, co-crystal or solvate thereof are administered simultaneously, separately or sequentially from each other.

In the kit-of-parts, the mode of administration and/or the method of administration of the present invention, the at least one chemotherapeutic agent is a chemotherapeutic agent suitable for use in treating breast cancer. In a further preferred embodiment of the kit-of-parts, the mode of administration and/or the method of administration of the present invention, the at least one chemotherapeutic agent is selected from anti-mitotic chemotherapeutic agents, nucleoside analog chemotherapeutic agents or tyrosine kinase inhibitors.

In other preferred embodiments of the kit-of-parts, the mode of administration and/or the method of administration of the present invention, the at least one chemotherapeutic agent is:
a) an anti-mitotic chemotherapeutic agent selected from taxanes and *vinca* alkaloids, more preferably an anti-mitotic chemotherapeutic agent selected from docetaxel, paclitaxel, vinorelbine, vinblastine, vindesine, vincristine, docosahexaenoic acid-paclitaxel, polyglutamate-paclitaxel and angiopep-paclitaxel;
b) a nucleoside analog chemotherapeutic agent selected from gemcitabine, cytarabine, fluorouracil and vidarabine; and/or
c) a tyrosine kinase inhibitor selected from dasatinib, nilotinib, bosutinib, ponatinib, bafetinib, imatinib, gefitinib, erlotinib and sunitinib.

In another preferred embodiment of the present invention, the at least one chemotherapeutic agent is docetaxel or vinorelbine. In yet another preferred embodiment of the present invention, according to any of the foregoing, the at least one chemotherapeutic agent is gemcitabine. In still another preferred embodiment of the present invention, according to any of the foregoing, the at least one chemotherapeutic agent is dasatinib.

Even more preferably, the at least one chemotherapeutic agent, according to any of the foregoing, is selected from docetaxel, gemcitabine or dasatinib. Alternatively, the at least one chemotherapeutic agent, according to any of the foregoing, is selected from docetaxel or gemcitabine.

Thus, one preferred embodiment relates to the kit-of-parts, the mode of administration and/or the method of administration of the present invention, wherein the at least one chemotherapeutic agent is selected from docetaxel, paclitaxel, vinorelbine, vinblastine, vindesine, vincristine, docosahexaenoic acid-paclitaxel, polyglutamate-paclitaxel, angiopep-paclitaxel, gemcitabine, cytarabine, fluorouracil, vidarabine, dasatinib, nilotinib, bosutinib or ponatinib.

Another preferred embodiment relates to relates to the kit-of-parts, the mode of administration and/or the method of administration of the present invention, wherein the at least one chemotherapeutic agent is selected from docetaxel, paclitaxel, gemcitabine, cytarabine, fluorouracil, dasatinib or nilotinib, more preferably from docetaxel, gemcitabine, fluorouracil, dasatinib or nilotinib, furthermore preferably from docetaxel, gemcitabine or dasatinib.

In a particularly preferred embodiment of the kit-of-parts, the mode of administration and/or the method of administration of the present invention, the molar ratio of the compound of the Formula (I) to the at least one chemotherapeutic agent is from 1:0.01 to 1:500. Preferably, the molar ratio of the compound of the Formula (I) to the at least one chemotherapeutic agent is from 1:0.05 to 1:200, more preferably 1:0.1 to 1:100, still more preferably 1:0.1 to 1:50. In a particularly preferred embodiment of the kit-of-parts, the mode of administration and/or the method of administration of the present invention, the at least one chemotherapeutic agent is:
a) the anti-mitotic chemotherapeutic agent, docetaxel, wherein the molar ratio of the compound of the Formula (I) to said anti-mitotic chemotherapeutic agent is from 1:0.05 to 1:1, yet more preferably 1:0.1 to 1:0.5;
b) the nucleoside analog chemotherapeutic agent, gemcitabine, wherein the molar ratio of the compound of the Formula (I) to said nucleoside analog chemotherapeutic agent is from 1:0.1 to 1:2, yet more preferably 1:0.1 to 1:1; and/or
c) the tyrosine kinase inhibitor, dasatinib, wherein the molar ratio of the compound of the Formula (I) to said tyrosine kinase inhibitor is from 1:0.1 to 1:2, yet more preferably 1:0.1 to 1:1.

In another particularly preferred embodiment of the foregoing, the present invention relates to a kit-of-parts, a mode of administration and/or a method of administration comprising a compound of the Formula (I) and vinorelbine, wherein the molar ratio of the compound of the Formula (I) to vinorelbine is 1:0.3.

Examples of the compositions of the present invention and representative processes for their isolation, use, and manufacture appear below, but should not be construed to limit the invention.

EXAMPLES

I) Material and Methods
a) Reagents and Antibodies

Cell culture media, fetal bovine serum (FBS) and tetramethylrhodamine ethyl ester (TMRE) were purchased from Invitrogen (Gaithersburg, Md.). Propidium iodide (PI) and 3-(4,5-dimethylthiazol-2-yl)-2,5-diphenyltetrazolium bromide (MTT) were from Sigma Chemical (St Louis, Mo., USA). Annexin V-FITC, Matrigel, Z-VAD-FMK, AC-IETD-AF and AC-DEVD-AFC were purchased from BD Biosciences (San Jose, Calif., USA). The compound of Formula (I), also referred to herein as F(I), was provided by EntreChem S.L. (Oviedo, Spain) and obtained according to the procedure described in J. Med. Chem. (2012) 55:5813-5825. Docetaxel was from Hospira UK Ltd (Warwickshire, UK). Vinorelbine was from Pierre Fabre (Barcelona, Spain). Gemcitabine was from Lilly (Madrid, Spain). Other generic chemicals were purchased from Sigma-Aldrich (St. Louis, Mo., USA), Roche Biochemicals, or Merck (Darmstadt, Germany).

b) Cell Culture

All cell lines were cultured at 37° C. in a humidified atmosphere in the presence of a mixture of 5% $CO_2$ and 95% air. Cells were grown in DMEM or in RPMI medium containing high glucose concentration (4,500 mg/liter) and antibiotics (penicillin at 100 mU/ml, streptomycin at 100 μg/ml) and supplemented with 10% FBS. Cell lines were provided by Drs. J. Losada and A. Balmain, (originally from Dr. J. W. Gray's Laboratory who in turn obtained them from the ATCC or from collections development in the laboratories of Drs. S. Ethier and A. Gazdar, to avoid errors occurring when obtained through "second-hand" sources) [Cancer Cell. (2006) 10:515-527]. Cell identities were verified by STR analyses [Oncogene (2014) 33:148-156].

c) Cell Proliferation, Cell Cycle and Apoptosis Assays

Cells were plated in 24-well plates at 10,000-20,000 cells/well and cultured overnight in DMEM or RPMI+10% FBS. The next day medium was replaced with DMEM or RPMI containing different concentrations of F(I). Cell proliferation was analyzed 48 and 72 hours later by an MTT-based assay as described in Cancer Res. (2005) 65:6801-6810. Unless otherwise indicated, the results are presented as the mean±standard deviation (SD) of quadruplicates of a representative experiment that was repeated at least three times.

To determine whether the combinations of F(I) with dasatinib, docetaxel, vinorelbine or gemcitabine were synergistic, additive, or antagonistic the CalcuSyn v2.0 software program (Biosoft, Ferguson, Mo.) was used as described in Mol. Cancer Ther. (2012) 11:1342-1352. Results are plotted as the mean±SD values of quadruplicates from two experiments.

For the analysis of the cell cycle profiles, cells were treated with F(I) during 48 hours and subsequently collected by pooling together the non-attached and attached cells. After washing with PBS, cells were fixed and permeabilized by ice-cold 70% ethanol overnight. Cells were centrifuged, resuspended in 500 μL of PBS containing 250 μg DNase-free RNAase A (Sigma-Aldrich) and incubated at room temperature for 2 hours. Then, 2.5 μg of propidium iodide (PI; Sigma-Aldrich) were added. DNA content and cell cycle analyses were performed by using a BD Accuri C6 flow cytometer and the C6 software (BD Biosciences).

d) Xenograft Studies

Mice were manipulated at the animal facility of the CIC in Salamanca following legal guidelines. Female BALB/c nu/nu mice (7 weeks old) were obtained from Charles River Laboratories (Wilmington, Mass., USA). A total of 5×106 MDA-MB231 cells in 100 μL of DMEM and 100 μL of Matrigel (BD Biosciences) were injected subcutaneously into the right and left flank of each mouse. When tumours reached a mean volume of 100 mm³, animals (n=32) were randomized into four groups (with equal average tumour volumes) (vehicle n=8, F(I) n=8, docetaxel n=8, and F(I)+ docetaxel n=8). Mice were treated every four days intravenously with 12 mg/kg of F(I), and weekly, intraperitoneally with docetaxel 15 mg/kg. Tumour diameters were serially measured by callipers twice per week and tumour volumes were calculated by the following formula: volume=width²× length/2. Mice were sacrificed on day 41. For biochemical and drug accumulation analyses, tumor samples were obtained after sacrifice of the animals by $CO_2$ inhalation, and 6 hours after being treated with the different drugs, and immediately frozen in liquid nitrogen. The tumors were minced, washed with PBS, and homogenized (Dispomix, L&M Biotech, Holly Springs, N.C., USA) in ice-cold lysis buffer (1.5 mL/100 mg tumor). This homogenate was centrifuged at 10,000×g for 20 minutes at 4° C., and the supernatants were transferred to new tubes.

d) Statistical Analyses

Comparisons of continuous variables between two groups for the mice tumor model experiments were performed using a two-sided Student's t-test. At least two independent experiments were performed for the in vivo studies. Differences were considered to be statistically significant when P values were less than 0.05. Statistical data are presented as the mean±SD. All data were analyzed using the statistical software SPSS 21.0 (SPSS Inc., Chicago, Ill.).

II) Results a) Effect of F(I) on TNBC Cell Lines.

Figure 1:
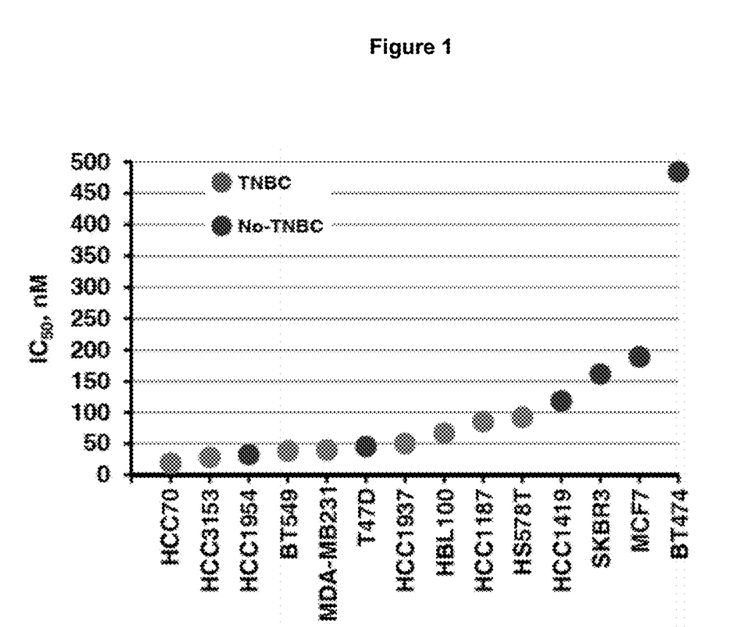
FIG. 1. $IC_{50}$ (nM) of F(I) on HCC-70, HCC-3153, BT549, MDA-MB-231 (MDAMB231), HCC-1937, HBL-100 (HBL100), HCC-1187 and HS578T triple-negative breast cancer cells (TNBC), as opposed to HCC1954, T47D, HCC1419, SKBR3, MCF7 and BT474 non-triple-negative breast cancer cells (No-TNBC).

To analyze the potential antineoplastic effect of F(I) on TNBC, its action on a panel of eight representative TNBC cell lines (HCC-70, HCC-3153, BT549, MDA-MB-231 (MDAMB231), HCC-1937, HBL-100 (HBL100), HCC-1187 and HS578T) using MTT metabolism as readout of the effect of F(I) on cell number was evaluated. Additionally tested as controls were a panel of six representative non-TNBC cell lines (HCC1954, T47D, HCC1419, SKBR3, MCF7 and BT474). Cells were plated and treated for 48 or 72 hours with different doses of F(I). Treatment with F(I) decreased MTT metabolism of all the TNBC cell lines studied in a dose-dependent and time-dependent manner (FIG. 1A). At 72 hours of treatment, F(I) $IC_{50}$ values for all cell lines was below 100 nM (FIG. 1B), indicating that F(I) was a potent inhibitor of MTT metabolism in TNBC cells.

b) In Vivo Antitumoral Effect of F(I).

Figure 2:
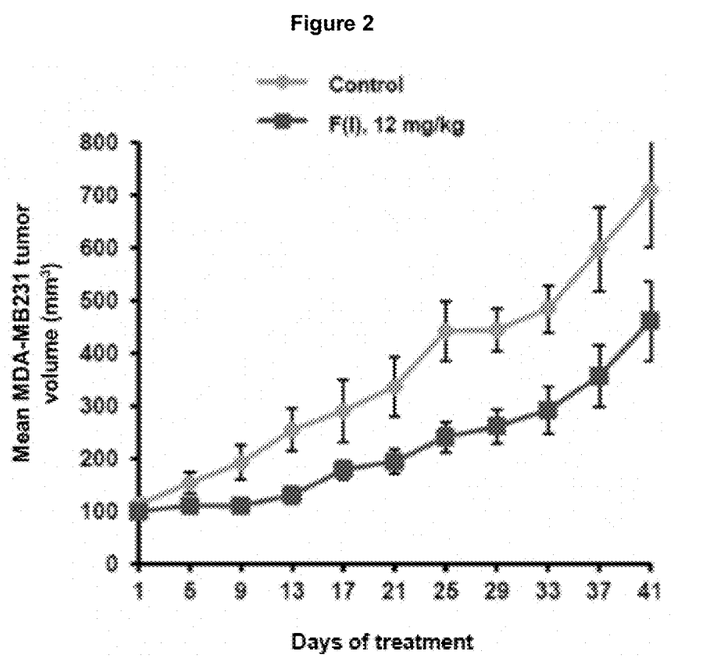
FIG. 2. Effect of F(I) over time on MDA-MB-231 (MDA-MB231) tumor volume in mice.
Figure 3:
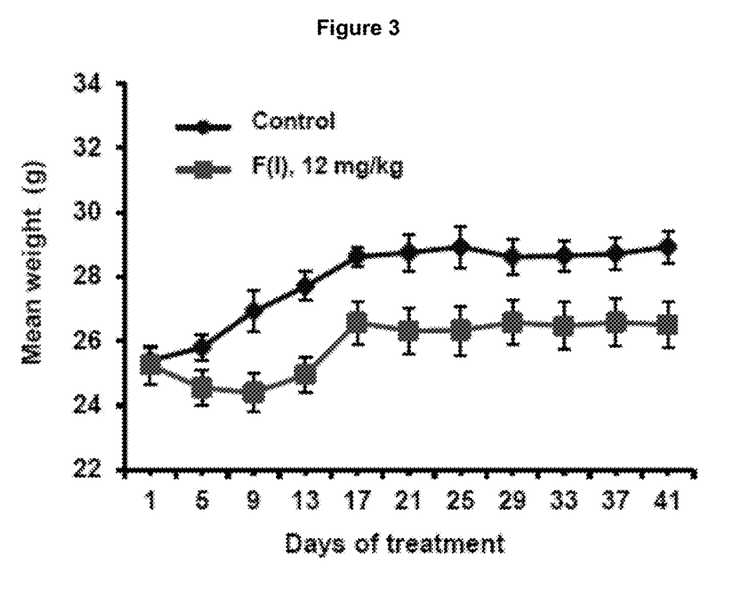
FIG. 3. Effect of F(I) over time on body weight of mice.

The potential in vivo antitumoral effect of F(I) was next investigated. Mice injected with MDA-MB231 cells in the caudal mammary fat pad developed tumors within two weeks from the date of injection. Once tumors established and reached a mean volume of 100 mm³, mice were randomized to receive vehicle or F(I) (12 mg/kg), intravenously every 3 days. Pharmacokinetic measurements of F(I) concentration in the tumors at 6 hours after the last treatment indicated that F(I) accumulated at doses higher that those deemed active in vitro (3.8 μg/g and 2.2 μg/g in two tumors from two different mice). Treatment with F(I) exerted an inhibitory effect on tumor growth (decrease in the growth of tumors, FIG. 2) developed from TNBC cells implanted in the mammary tissue of mice. Body weight showed a slight decrease initially in animals treated with F(I), which recovered later (FIG. 3).

c) F(I) Synergizes with Standard of Care Drugs In Vitro and In Vivo.

To explore whether F(I) potentiated the action of drugs used in the therapy of TNBC, drug combination experiments were performed, and the results analyzed by the Chou and Talalay algorithm [Adv. Enzyme Regul. (1984) 22:27-55] which is used to determine whether a drug combination is synergistic, additive or antagonistic or has no effect. The results are presented in part in Tables 1 to 7, wherein CI refers to the combination index and s.d. refers to the standard deviation from the mean.

Figure 4:
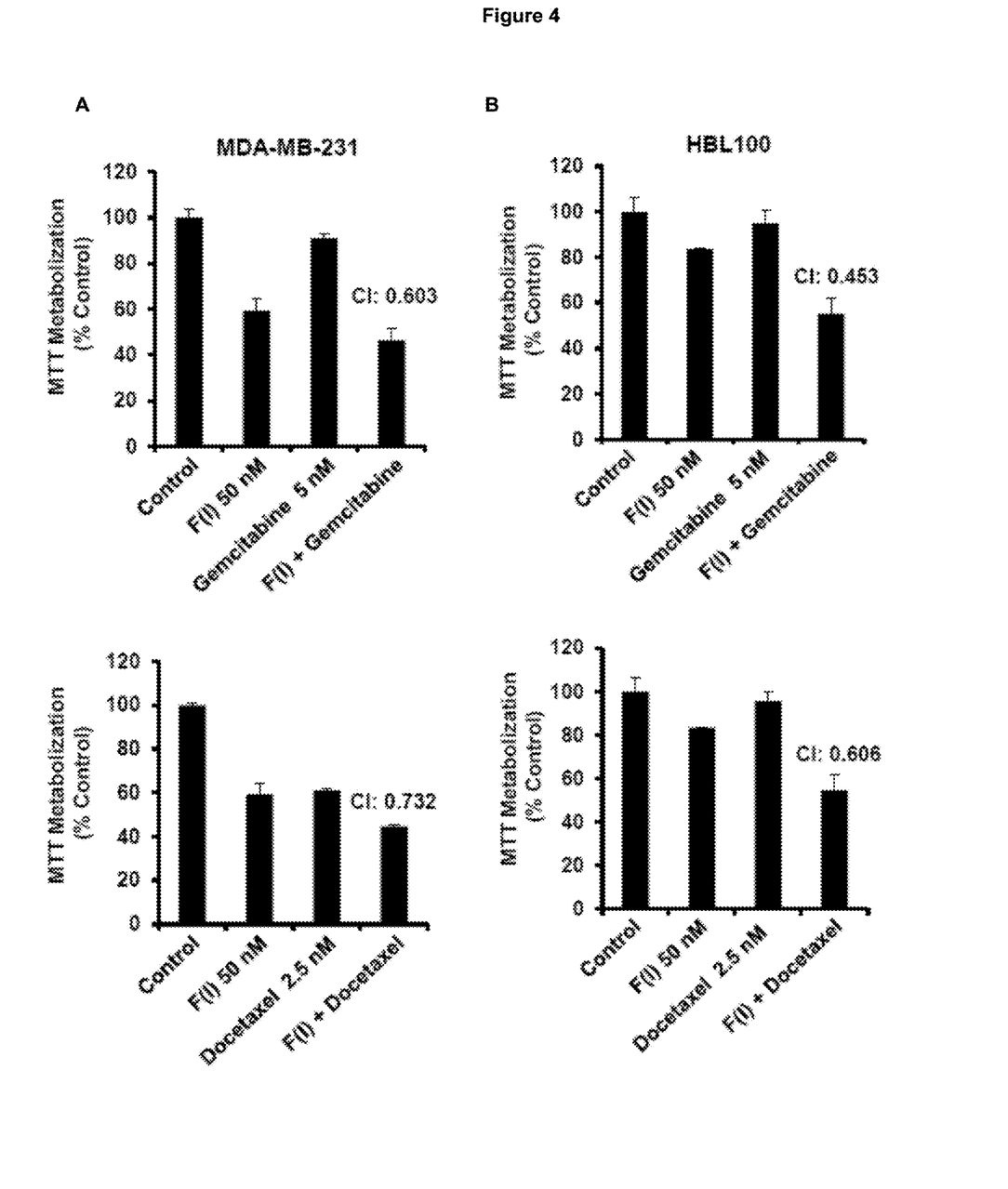
FIG. 4. Anti-proliferative effect on A. MDA-MB-231 and B. HBL-100 (HBL100) cells, measured as percentage of MTT metabolism (metabolization) with respect to an untreated control (CTRL, for which the mean absorbance values of untreated samples from each cell line were taken as 100%) of F(I) (50 nM), Gemcitabine (5 nM), and the corresponding combination thereof [F(I)+Gem.], top; and F(I) (50 nM), Docetaxel (2.5 nM), and the corresponding combination thereof [F(I)+Doc.], bottom.
Figure 5:
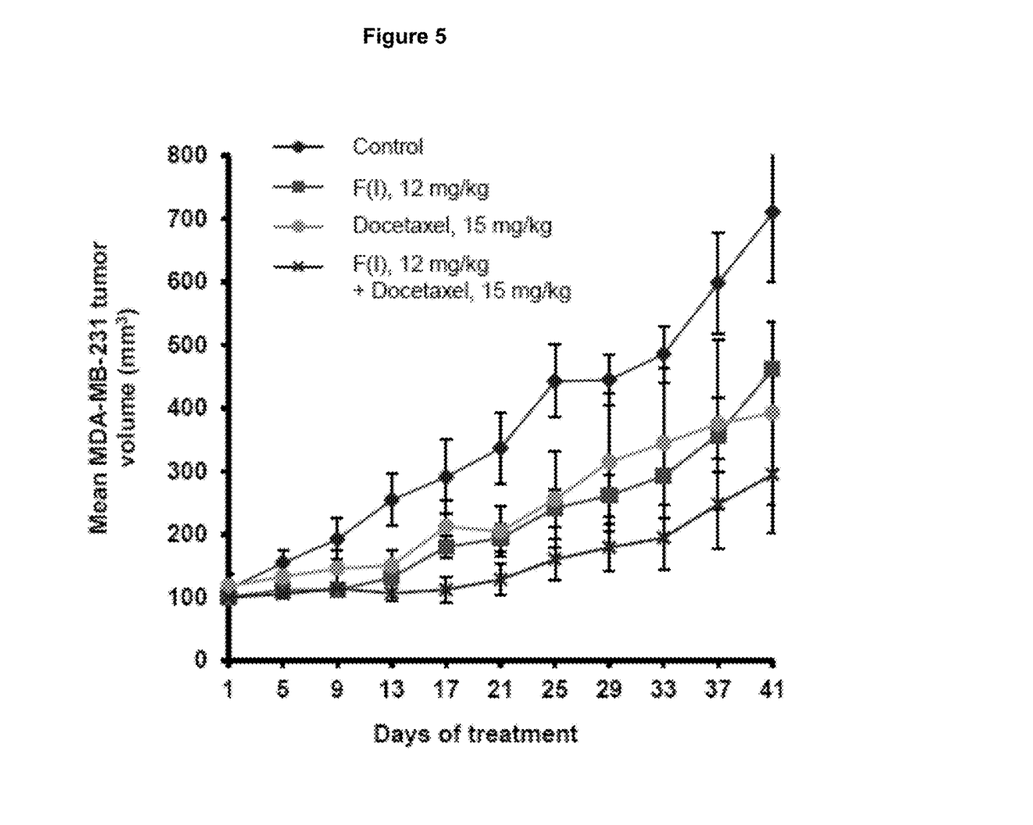
FIG. 5. Effect overtime on MDA-MB-231 tumor volume in mice treated with F(I) (12 mg/kg), Docetaxel (15 mg/kg), and a combination thereof [F(I) (12 mg/kg)+Docetaxel (15 mg/kg)].
Figure 6:
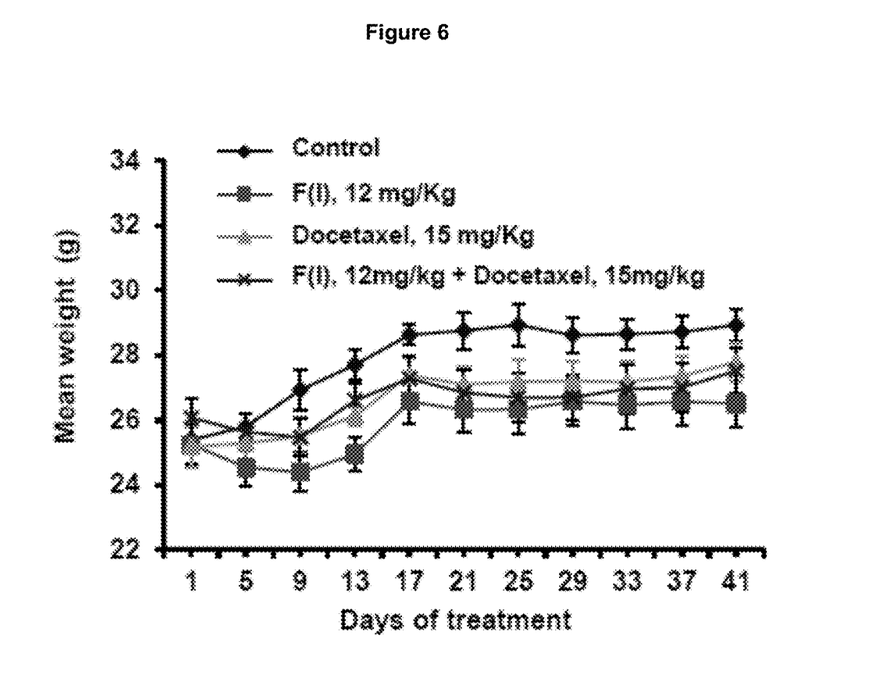
FIG. 6. Effect over time on body weight of mice treated with F(I) (12 mg/kg), Docetaxel (15 mg/kg), and a combination thereof [F(I) (12 mg/kg)+Docetaxel (15 mg/kg)].

The aforementioned experiments indicated that F(I) augmented the action of several drugs used in the treatment of TNBC. In particular, F(I) favored the efficacy of taxanes in vitro and in vivo, and gemcitabine in vitro, two drugs currently used clinically in the treatment of TNBC. Moreover, synergy was observed with docetaxel and gemcitabine (FIGS. 4A and 4B), while the action of vinorelbine was not clearly augmented by F(I) except at the particular molar ratio of each drug shown in Table 4. In vivo evaluation of the effect of F(I) in combination with docetaxel was also performed on MDA-MB-231 xenografted tumors in mice (FIG. 5). As shown in FIG. 5, the combination of F(I) had a stronger antitumoral effect than the individual treatments. Body weights of animals treated with these drugs or their combination were not substantially modified by the treatments (FIG. 6), suggesting that F(I), either alone or in combination with other anti-cancer chemotherapeutic agents, was well tolerated.

TABLE 1

Effect of F(I), Dasatinib and combinations thereof on inhibition of MDA-MB-231 cell proliferation.

| Quantity of drug | | | | MTT metabolism | | | | | |
|---|---|---|---|---|---|---|---|---|---|
| | | | | Assay 1 | | | Assay 2 | | |
| F(I) (nM) | Dasatinib (μM) | F(I) (nM) + Dasatinib (μM) | Ratio F(I)/Dasatinib | mean (%) | s.d. | CI | mean (%) | s.d. | CI |
| 0 | 0 | 0 | — | 100 | 0.048 | — | 100 | 0.031 | — |
| 10 | 0 | 10 | — | 94.27 | 0.011 | — | 96.65 | 0.009 | — |
| 50 | 0 | 50 | — | 70.05 | 0.007 | — | 59.26 | 0.049 | — |
| 0 | 0.5 | 0 + 0.5 | 0 | 65.29 | 0.002 | — | 62.89 | 0.041 | — |
| 10 | 0.5 | 10 + 0.5 | 0.02 | 59.97 | 0.027 | 0.76 | 57.95 | 0.035 | 0.55 |
| 50 | 0.5 | 50 + 0.5 | 0.1 | 56.79 | 0.053 | 1.19 | 47.05 | 0.046 | 0.61 |
| 0 | 1.0 | 0 + 1.0 | 0 | 59.58 | 0.008 | — | 63.07 | 0.013 | — |
| 10 | 1.0 | 10 + 1.0 | 0.01 | 53.87 | 0.020 | 0.73 | 54.75 | 0.016 | 0.66 |
| 50 | 1.0 | 50 + 1.0 | 0.05 | 50.31 | 0.034 | 0.97 | 41.79 | 0.033 | 0.51 |
| 0 | 2.0 | 0 + 2.0 | 0 | 56.05 | 0.024 | — | 55.89 | 0.046 | — |
| 10 | 2.0 | 10 + 2.0 | 0.005 | 52.88 | 0.018 | 1.19 | 54.16 | 0.022 | 1.09 |
| 50 | 2.0 | 50 + 2.0 | 0.025 | 45.90 | 0.002 | 0.96 | 42.25 | 0.019 | 0.63 |

TABLE 2

Effect of F(I), Gemcitabine and combinations thereof on inhibition of MDA-MB-231 cell proliferation.

| Quantity of drug | | | | MTT metabolism | | | | | |
|---|---|---|---|---|---|---|---|---|---|
| | | | | Assay 1 | | | Assay 2 | | |
| F(I) (nM) | Gemcitabine (nM) | F(I) (nM) + Gemcitabine (nM) | Ratio F(I)/Gemcitabine | mean (%) | s.d. | CI | mean (%) | s.d. | CI |
| 0 | 0 | 0 | — | 100 | 0.025 | — | 100 | 0.034 | — |
| 10 | 0 | 10 | — | 94.27 | 0.011 | — | 96.65 | 0.009 | — |
| 50 | 0 | 50 | — | 70.05 | 0.007 | — | 59.26 | 0.049 | — |
| 0 | 5 | 0 + 5 | 0 | 77.29 | 0.032 | — | 90.99 | 0.018 | — |
| 10 | 5 | 10 + 5 | 2 | 75.60 | 0.035 | 1.33 | 82.08 | 0.015 | 0.93 |
| 50 | 5 | 50 + 5 | 10 | 60.21 | 0.045 | 1.30 | 46.39 | 0.048 | 0.60 |
| 0 | 10 | 0 + 10 | 0 | 67.76 | 0.029 | — | 84.33 | 0.018 | — |
| 10 | 10 | 10 + 10 | 1 | 66.52 | 0.029 | 1.27 | 73.90 | 0.026 | 0.90 |
| 50 | 10 | 50 + 10 | 5 | 45.10 | 0.020 | 0.77 | 42.39 | 0.037 | 0.61 |
| 0 | 20 | 0 + 20 | 0 | 48.14 | 0.048 | — | 64.95 | 0.009 | — |
| 10 | 20 | 10 + 20 | 0.5 | 42.39 | 0.024 | 0.67 | 59.89 | 0.014 | 0.83 |
| 50 | 20 | 50 + 20 | 2.5 | 36.84 | 0.018 | 0.72 | 36.83 | 0.005 | 0.63 |

TABLE 3

Effect of F(I), Docetaxel and combinations thereof on inhibition of MDA-MB-231 cell proliferation.

| Quantity of drug | | | | MTT metabolism | | | | | |
|---|---|---|---|---|---|---|---|---|---|
| | | | | Assay 1 | | | Assay 2 | | |
| F(I) (nM) | Docetaxel (nM) | F(I) (nM) + Docetaxel (nM) | Ratio F(I)/Docetaxel | mean (%) | s.d. | CI | mean (%) | s.d. | CI |
| 0 | 0 | 0 | — | 100 | 0.049 | — | 100 | 0.012 | — |
| 10 | 0 | 10 | — | 94.27 | 0.011 | — | 96.65 | 0.009 | — |
| 50 | 0 | 50 | — | 70.05 | 0.007 | — | 59.26 | 0.049 | — |
| 0 | 2.5 | 0 + 2.5 | 0 | 84.46 | 0.016 | — | 60.92 | 0.009 | — |
| 10 | 2.5 | 10 + 2.5 | 4 | 84.27 | 0.003 | 1.72 | 61.36 | 0.042 | 0.56 |
| 50 | 2.5 | 50 + 2.5 | 20 | 71.70 | 0.041 | 2.31 | 44.73 | 0.008 | 0.73 |
| 0 | 5 | 0 + 5 | 0 | 69.03 | 0.015 | — | 51.36 | 0.020 | — |
| 10 | 5 | 10 + 5 | 2 | 61.10 | 0.036 | 0.92 | 46.47 | 0.026 | 0.64 |
| 50 | 5 | 50 + 5 | 10 | 50.47 | 0.014 | 1.12 | 36.82 | 0.014 | 0.78 |
| 0 | 10 | 0 + 10 | 0 | 38.17 | 0.033 | — | 44.50 | 0.038 | — |
| 10 | 10 | 10 + 10 | 0.5 | 33.20 | 0.017 | 0.76 | 40.67 | 0.007 | 1.02 |
| 50 | 10 | 50 + 10 | 2.5 | 30.90 | 0.021 | 0.87 | 30.45 | 0.020 | 0.99 |

TABLE 4

Effect of F(I), Vinorelbine and combinations thereof on inhibition of MDA-MB-231 cell proliferation.

| Quantity of drug | | | | MTT metabolism (%) | | | | | |
|---|---|---|---|---|---|---|---|---|---|
| | | | | Assay 1 | | | Assay 2 | | |
| F(I) (nM) | Vinorelbine (nM) | F(I) (nM) + Vinorelbine (nM) | Ratio F(I)/Vinorelbine | mean (%) | s.d. | CI | mean (%) | s.d. | CI |
| 0 | 0 | 0 | — | 100 | 0.044 | — | 100 | 0.012 | — |
| 10 | 0 | 10 | — | 94.27 | 0.011 | — | 96.65 | 0.009 | — |
| 50 | 0 | 50 | — | 70.05 | 0.007 | — | 59.26 | 0.049 | — |
| 0 | 1 | 0 + 1 | 0 | 94.11 | 0.026 | — | 73.02 | 0.047 | — |
| 10 | 1 | 10 + 1 | 10 | 90.82 | 0.008 | 2.80 | 72.02 | 0.016 | 1.09 |
| 50 | 1 | 50 + 1 | 50 | 64.44 | 0.038 | 1.28 | 77.00 | 0.010 | 3.13 |
| 0 | 3 | 0 + 3 | 0 | 84.61 | 0.009 | — | 71.99 | 0.020 | — |
| 10 | 3 | 10 + 3 | 3.33 | 73.52 | 0.137 | 0.88 | 63.11 | 0.014 | 1.29 |
| 50 | 3 | 50 + 3 | 16.6 | 62.30 | 0.039 | 1.32 | 75.78 | 0.023 | 5.25 |
| 0 | 5 | 0 + 5 | 0 | 84.42 | 0.036 | — | 56.42 | 0.001 | — |
| 10 | 5 | 10 + 5 | 2 | 73.29 | 0.028 | 1.19 | 56.25 | 0.004 | 1.19 |
| 50 | 5 | 50 + 5 | 10 | 58.91 | 0.011 | 1.25 | 67.44 | 0.050 | 3.79 |

TABLE 5

Effect of F(I), Dasatinib and combinations thereof on inhibition of HBL-100 cell proliferation.

| Quantity of drug | | | | MTT metabolism | | | | | |
|---|---|---|---|---|---|---|---|---|---|
| | | | | Assay 1 | | | Assay 2 | | |
| F(I) (nM) | Dasatinib (μM) | F(I) (nM) + Dasatinib (μM) | Ratio F(I)/Dasatinib | mean (%) | s.d. | CI | mean (%) | s.d. | CI |
| 0 | 0 | 0 | — | 100 | 0.044 | — | 100 | 0.019 | — |
| 10 | 0 | 10 | — | 85.52 | 0.005 | — | 99.53 | 0.006 | — |
| 50 | 0 | 50 | — | 66.35 | 0.041 | — | 62.85 | 0.030 | — |
| 0 | 0.5 | 0 + 0.5 | 0 | 61.25 | 0.019 | — | 65.30 | 0.021 | — |
| 10 | 0.5 | 10 + 0.5 | 0.02 | 63.31 | 0.020 | 3.61 | 60.77 | 0.025 | 0.53 |
| 50 | 0.5 | 50 + 0.5 | 0.1 | 59.33 | 0.004 | 2.10 | 52.37 | 0.015 | 0.65 |
| 0 | 1.0 | 0 + 1.0 | 0 | 61.08 | 0.022 | — | 64.94 | 0.014 | — |
| 10 | 1.0 | 10 + 1.0 | 0.01 | 60.23 | 0.015 | 1.52 | 59.09 | 0.050 | 0.72 |
| 50 | 1.0 | 50 + 1.0 | 0.05 | 55.60 | 0.036 | 1.48 | 45.51 | 0.026 | 0.53 |
| 0 | 2.0 | 0 + 2.0 | 0 | 58.58 | 0.019 | — | 58.48 | 0.025 | — |
| 10 | 2.0 | 10 + 2.0 | 0.005 | 52.03 | 0.037 | 0.25 | 57.36 | 0.011 | 1.00 |
| 50 | 2.0 | 50 + 2.0 | 0.025 | 51.46 | 0.005 | 1.10 | 45.78 | 0.011 | 0.60 |

TABLE 6

Effect of F(I), Gemcitabine and combinations thereof on inhibition of HBL-100 cell proliferation.

| Quantity of drug | | | | MTT metabolism | | | | | |
|---|---|---|---|---|---|---|---|---|---|
| | | | | Assay 1 | | | Assay 2 | | |
| F(I) (nM) | Gemcitabine (nM) | F(I) (nM) + Gemcitabine (nM) | Ratio F(I)/Gemcitabine | mean (%) | s.d. | CI | mean (%) | s.d. | CI |
| 0 | 0 | 0 | — | 100 | 0.044 | — | 100 | 0.019 | — |
| 10 | 0 | 10 | — | 85.52 | 0.005 | — | 99.53 | 0.006 | — |
| 50 | 0 | 50 | — | 66.35 | 0.041 | — | 62.85 | 0.030 | — |
| 0 | 5 | 0 + 5 | 0 | 90.75 | 0.193 | — | 88.93 | 0.039 | — |
| 10 | 5 | 10 + 5 | 2 | 95.70 | 0.037 | 24.21 | 86.28 | 0.009 | 0.75 |
| 50 | 5 | 50 + 5 | 10 | 65.59 | 0.033 | 2.83 | 55.51 | 0.035 | 0.77 |
| 0 | 10 | 0 + 10 | 0 | 85.93 | 0.040 | — | 83.52 | 0.030 | — |
| 10 | 10 | 10 + 10 | 1 | 83.15 | 0.024 | 3.47 | 85.26 | 0.046 | 1.14 |
| 50 | 10 | 50 + 10 | 5 | 59.86 | 0.049 | 2.14 | 50.34 | 0.033 | 0.84 |
| 0 | 20 | 0 + 20 | 0 | 61.98 | 0.045 | — | 80.59 | 0.003 | — |
| 10 | 20 | 10 + 20 | 0.5 | 62.46 | 0.010 | 1.20 | 68.21 | 0.023 | 1.11 |
| 50 | 20 | 50 + 20 | 2.5 | 54.30 | 0.009 | 1.81 | 40.21 | 0.014 | 0.89 |

TABLE 7

Effect of F(I), Docetaxel and combinations thereof on inhibition of HBL-100 cell proliferation.

| Quantity of drug | | | | MTT metabolism | | | | | |
|---|---|---|---|---|---|---|---|---|---|
| | | | | Assay 1 | | | Assay 2 | | |
| F(I) (nM) | Docetaxel (nM) | F(I) (nM) + Docetaxel (nM) | Ratio F(I)/Docetaxel | mean (%) | s.d. | CI | mean (%) | s.d. | CI |
| 0 | 0 | 0 | — | 100 | 0.044 | — | 100 | 0.019 | — |
| 10 | 0 | 10 | — | 85.52 | 0.005 | — | 99.53 | 0.006 | — |
| 50 | 0 | 50 | — | 66.35 | 0.041 | — | 62.85 | 0.030 | — |
| 0 | 2.5 | 0 + 2.5 | 0 | 96.93 | 0.035 | — | 83.41 | 0.037 | — |
| 10 | 2.5 | 10 + 2.5 | 4 | 91.79 | 0.023 | 8.20 | 85.06 | 0.017 | 0.84 |
| 50 | 2.5 | 50 + 2.5 | 20 | 65.69 | 0.040 | 2.88 | 55.70 | 0.038 | 0.84 |
| 0 | 5 | 0 + 5 | 0 | 85.11 | 0.005 | — | 70.61 | 0.042 | — |
| 10 | 5 | 10 + 5 | 2 | 73.09 | 0.009 | 1.53 | 65.52 | 0.034 | 0.75 |
| 50 | 5 | 50 + 5 | 10 | 60.73 | 0.004 | 2.35 | 48.41 | 0.029 | 0.92 |
| 0 | 10 | 0 + 10 | 0 | 55.03 | 0.050 | — | 54.59 | 0.024 | — |
| 10 | 10 | 10 + 10 | 0.5 | 53.50 | 0.007 | 0.98 | 54.42 | 0.028 | 1.05 |
| 50 | 10 | 50 + 10 | 2.5 | 46.42 | 0.009 | 1.41 | 39.26 | 0.027 | 1.08 |

Globally, combination of the mithramycin analogues with chemotherapy agents as per the present invention produced a synergic increase in antitumoral effect in the treatment of TNBC, and such synergic combinations have been shown to be stable in in vivo models, thereby rendering said synergic combinations suitable for use in the clinical setting and hence, industrially applicable.

The invention claimed is:

1. A composition comprising:
   a) a compound of Formula (I),

Formula (I)

or a salt, co-crystal or solvate thereof; and
   b) at least one chemotherapeutic agent, or a salt, co-crystal or solvate thereof, wherein said at least one chemotherapeutic agent is:
      i) the anti-mitotic chemotherapeutic agent, docetaxel, wherein the molar ratio of the compound of the Formula (I) to said anti-mitotic chemotherapeutic agent is from 1:0.05 to 1:1;
      ii) the nucleoside analog chemotherapeutic agent, gemcitabine, wherein the molar ratio of the compound of the Formula (I) to said nucleoside analog chemotherapeutic agent is from 1:0.1 to 1:2;
      iii) the tyrosine kinase inhibitor, dasatinib, wherein the molar ratio of the compound of the Formula (I) to said tyrosine kinase inhibitor is from 1:0.1 to 1:2; and/or
      iv) vinorelbine, wherein the molar ratio of the compound of Formula (I) to vinorelbine is 1:0.3.

2. A composition according to claim 1, wherein the at least one chemotherapeutic agent is the anti-mitotic chemotherapeutic agent docetaxel.

3. A composition according to claim 1, wherein the at least one chemotherapeutic agent is the nucleoside analog chemotherapeutic agent gemcitabine.

4. A composition according to claim 1, wherein the at least one chemotherapeutic agent is the tyrosine kinase inhibitor dasatinib.

5. A kit-of-parts for use in treating triple negative breast cancer comprising:
   a) a compound of Formula (I), Formula (I)

or a salt, co-crystal or solvate thereof; and
   b) at least one chemotherapeutic agent, or a salt, co-crystal or solvate thereof, wherein said at least one chemotherapeutic agent is:
      i) the anti-mitotic chemotherapeutic agent, docetaxel, wherein the molar ratio of the compound of the Formula (I) to said anti-mitotic chemotherapeutic agent is from 1:0.05 to 1:1;
      ii) the nucleoside analog chemotherapeutic agent, gemcitabine, wherein the molar ratio of the compound of the Formula (I) to said nucleoside analog chemotherapeutic agent is from 1:0.1 to 1:2;
      iii) the tyrosine kinase inhibitor, dasatinib, wherein the molar ratio of the compound of the Formula (I) to said tyrosine kinase inhibitor is from 1:0.1 to 1:2; and/or iv) vinorelbine, wherein the molar ratio of the compound of the Formula (I) to vinorelbine is 1:0.3.

6. A method for producing a composition according to claim 1, which comprises mixing:
a) a compound of Formula (I), Formula (I)

or a salt, co-crystal or solvate thereof; and
b) at least one chemotherapeutic agent, or a salt, co-crystal or solvate thereof, wherein said at least one chemotherapeutic agent is:
  i) the anti-mitotic chemotherapeutic agent, docetaxel, wherein the molar ratio of the compound of the Formula (I) to said anti-mitotic chemotherapeutic agent is from 1:0.05 to 1:1;
  ii) the nucleoside analog chemotherapeutic agent, gemcitabine, wherein the molar ratio of the compound of the Formula (I) to said nucleoside analog chemotherapeutic agent is from 1:0.1 to 1:2;
  iii) the tyrosine kinase inhibitor, dasatinib, wherein the molar ratio of the compound of the Formula (I) to said tyrosine kinase inhibitor is from 1:0.1 to 1:2; and/or
  iv) vinorelbine, wherein the molar ratio of the compound of the Formula (I) to vinorelbine is 1:0.3.

7. A method of preventing and/or treating breast cancer by administering to a patient a composition according to claim 1.

8. A method of treating triple negative breast cancer by administering to a subject in need thereof: a compound of Formula (I), Formula (I)

or a salt, co-crystal or solvate thereof; and
at least one chemotherapeutic agent, or a salt, co-crystal or solvate thereof, wherein said at least one chemotherapeutic agent is:
  i) the anti-mitotic chemotherapeutic agent, docetaxel, wherein the molar ratio of the compound of the Formula (I) to said anti-mitotic chemotherapeutic agent is from 1:0.05 to 1:1;
  ii) the nucleoside analog chemotherapeutic agent, gemcitabine, wherein the molar ratio of the compound of the Formula (I) to said nucleoside analog chemotherapeutic agent is from 1:0.1 to 1:2;
  iii) the tyrosine kinase inhibitor, dasatinib, wherein the molar ratio of the compound of the Formula (I) to said tyrosine kinase inhibitor is from 1:0.1 to 1:2; and/or
  iv) vinorelbine, wherein the molar ratio of the compound of the Formula (I) to vinorelbine is 1:0.3,
wherein said compound of Formula (I), or a salt, co-crystal or solvate thereof, and said at least one chemotherapeutic agent, or a salt, co-crystal or solvate thereof are administered simultaneously, separately or sequentially from each other.

* * * * *